United States Patent [19]

Mirviss

[11] Patent Number: 4,501,903

[45] Date of Patent: Feb. 26, 1985

[54] CHLOROMETHYLATION PROCESS

[75] Inventor: Stanley B. Mirviss, Stamford, Conn.

[73] Assignee: Stauffer Chemical Company, Westport, Conn.

[21] Appl. No.: 511,073

[22] Filed: Jul. 5, 1983

[51] Int. Cl.³ .......................................... C07D 333/12
[52] U.S. Cl. ................................................... 549/29
[58] Field of Search .......................................... 549/29

[56] References Cited

U.S. PATENT DOCUMENTS

| | | | |
|---|---|---|---|
| 2,527,680 | 10/1950 | Kyrides et al. | 549/29 |
| 3,271,465 | 9/1966 | Krewer et al. | 549/29 |
| 3,284,518 | 11/1966 | Ayers et al. | 549/29 |

FOREIGN PATENT DOCUMENTS

37-9585  7/1962  Japan ...................................... 549/29

*Primary Examiner*—Robert T. Bond
*Attorney, Agent, or Firm*—Vivienne T. White

[57] ABSTRACT

The invention is a method of increasing the yield of chloromethylthiophene produced by the addition of concentrated aqueous formaldehyde solution to a mixture of thiophene and concentrated hydrochloric acid and passing in a rapid stream of gaseous hydrogen chloride. The improvement comprises increasing the rate of addition of the gaseous hydrogen chloride from about 0.6 moles per mole of thiophene per hour to about 1.5 moles per mole of thiophene per hour to increase product yield.

8 Claims, No Drawings

CHLOROMETHYLATION PROCESS

BACKGROUND OF THE INVENTION

1. Field of the Invention

The invention relates to the chloromethylation of aromatic compounds and in particular to the chloromethylation of sulfur containing compounds, such as thiophene, to produce 2-chloromethylthiophene used as an intermediate in the production of thiophene 2-acetonitrile.

2. Related Art

Chloromethylation, i.e., the replacement of a hydrogen atom by a chloromethyl group is a known reaction. A commonly found method involves the use of formaldehyde and hydrogen chloride in the presence of a converting agent such as zinc chloride. Various methods of conducting the chloroalkylation of sulfur-containing hydrocarbons have been disclosed, see U.S. Pat. Nos. 2,527,679; 2,541,408 and 2,951,000.

In particular 2-chloromethylthiophene (CMT) has been prepared by the addition of a concentrated aqueous formaldehyde solution to a mixture of thiophene and concentrated hydrochloric acid and passing in a rapid stream of hydrogen chloride. This batch process is said to require strict constraints on hydrogen chloride gassing rates and heat removal to maximize yields. With no equipment constraints, however, the hydrogen chloride addition rate remains limited on the low side by a 6 hour maximum reaction time in a temperature range of $-20°$ C. to $+10°$ C. Long reaction times cause the system to foul. The fouling is caused by the formation of polymeric or oligomeric material of high viscosity such as thiophene formaldehyde oligomers. When this happens the reaction mixture is highly emulsified and the product, 2-chloromethylthiophene, will not separate out even with a deemulsification agent. High hydrogen chloride addition rates were also thought to be limited by formation of high temperature zones, which also favored oligomeric by-product formation and caused the system to foul. The heat to be removed is generally a function of the gassing rate and the desired temperature path over the reaction time. A normal plant reactor system consisting of a vessel, pump and cooler further limit the hydrogen chloride gassing range by its design characteristics.

An object of the invention is to provide a means of increasing the yield of the desired chloromethylated product with time and to minimize the formation of thiophene-formaldehyde oligomers which contain the poly(thienyl methane), or

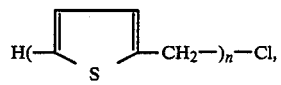

structure.

SUMMARY OF THE INVENTION

A process of increasing the yield of the chloromethylated product and in particular a mono-chloromethylated thiophene product with time has been discovered. The process not only increases the reaction rate but advantageously increases the yield per batch.

It was unexpectedly discovered that increasing the addition rate of the hydrogen chloride gas to from about 0.6 mole of gaseous hydrogen chloride per mole of thiophene per hour to about 1.5 moles of gaseous hydrogen chloride per mole of thiophene per hour greatly increased the yield of 2-chloromethylthiophene in contradistinction to the prior art.

DETAILED DESCRIPTION OF THE INVENTION

It was discovered that the increased rate of addition of gaseous hydrogen chloride increased the yield of chloromethylthiophene obtained by about 6%. In the practice of the invention as disclosed herein an increased addition rate of from about 0.6 mole of gaseous hydrogen chloride per mole of thiophene per hour to about 1.5 moles of gaseous hydrogen chloride per mole of thiophene per hour produced increased yields of the chloromethylthiophene product. A rate of addition of about 1 mole of gaseous hydrogen chloride per mole of thiophene is preferred.

Chloromethylthiophene is generally produced in a batchwise process utilizing one or more independent reactors having separate cooling means and separate hydrogen chloride gassing means, wherein strict reaction temperature conditions and hydrogen chloride gassing rates are maintained.

In the process of the invention for producing chloromethylthiophene, a jacketed reactor having additional external cooling means connected thereto is charged with dilute or concentrated hydrochloric acid, thiophene and paraformaldehyde under strict low temperature conditions (generally less than about 0° C. regulated by circulating through the cooling means). Temperatures of $-20°$ C. to about $+5°$ C. are suitable for use in the practice of the invention. Thereafter an amount of hydrogen chloride gas is supplied through the cooling means at a specific feed rate and temperature to the circulating reactor mixture to cause the addition of the gas to be accomplished at a rate necessary to increase the yield of chloromethylthiophene. Generally, the addition rate should be such as to be completed in from about 1 to about 2.5 hours. Alternatively, the hydrogen chloride can be added to the reaction mixture by means of a gas sparger or dispenser with good agitation in the reactor.

Increasing the addition rate of the gaseous hydrogen chloride advantageously was found to increase the yield of 2-chloromethylthiophene.

In the practice of the invention, generally from about 2.5 to 3.5 moles of gaseous and aqueous hydrogen chloride is combined with a mole of thiophene and from about 0.9 to about 1.5 moles of formaldehyde to produce the chloromethylthiophene product.

The above amounts are preferable for conducting the reaction in which the total HCl amounts are supplied in the form of aqueous hydrochloric acid and gaseous hydrogen chloride. It was observed that at about a 4.0 mole total hydrogen chloride addition per mole of thiophene the chloromethylthiophene yield decreased with increasing polymer formation.

Generally about half of the total hydrogen chloride is added to the reaction mixture as gaseous hydrogen chloride with about half of the total aqueous hydrochloric acid. Increasing the amount of gaseous HCl at the expense of aqueous hydrogen chloride did not appreciably affect the chloromethylthiophene yield but did increase the amount of polymer product at the expense of unreacted thiophene. Increasing the amount of aqueous hydrogen chloride, however, gives low CMT, low by-products yield and high amounts of unreacted thiophene.

At higher total hydrogen chloride amounts (e.g., >4.0 moles per mole of thiophene), increasing gaseous hydrogen chloride at the expense of aqueous HCl decreased CMT yield with increased yield of polymeric material.

A range of about 2.5 to about 4.0 moles of total hydrogen chloride per mole of thiophene is within the scope of the invention with a molar ratio of from about 2.75 to 3.75 total hydrogen chloride per mole of thiophene being preferred. A molar ratio of gaseous hydrogen chloride to aqueous hydrogen chloride of from about 0.65 to about 1.45 is recommended with a ratio of from about 0.8:1 to about 1.35:1 being preferred.

The aqueous hydrogen chloride concentration should be from about 22% to about 42% for practicing the invention. A concentration of from about 27% to about 38% is preferred.

After the hydrogen chloride is added, the reactor contents are additionally stirred and maintained at from about −20° C. to about +5° C. and preferably from about −10° C. to about 0° C. for a period of time necessary to complete the reaction. A total reaction time before quenching the reaction of at least 2.3 hours and not more than 6 hours is generally acceptable with a preferred range being about 4-5 hours. For example if the hydrogen chloride gas addition time is 1.5-2 hours, the additional reaction time would be preferably 1.5-3.5 hours, but not more than 6 hours total reaction time. The process thereafter is as described in the prior art, in that the 2-chloromethylthiophene product is recovered by the addition of water and a commercial deemulsifier after which the contents of the reactor are allowed to settle and the product layer then separated. Increased yield of the chloromethylthiophene product is obtained by the disclosed method. Yields of from about 68% to about 72% based on the thiophene charged have been obtained utilizing the process of the invention. These yields are to be compared with 57%-63% yields when the hydrogen chloride gas is added over the entire reaction time. Generally a reaction time of from about 3 to 5 hours is required.

It is a requirement of the process that the fast hydrogen chloride gas addition period be followed by the above additional stirring period. If this is not done, the yield of product is sharply curtailed, i.e., the yield is 32-40% for 1.5 hours hydrogen chloride addition time with no subsequent reaction time compared with the afore-cited 68-72% yield when additional reaction time is provided. An additional reaction time of about 1.5 to 2.5 hours is generally required.

There is no complete explanation for the increased yield. However, it is apparent from the examples provided that there is a greater thiophene conversion and that there is less polymer formed. It is postulated that the high concentration of hydrogen chloride competes more effectively for the thenyl or thienylmethyl carbonium ion $C_5H_3SCH_2\oplus$ (positive ion), formed by the reaction of protonated formaldehyde and thiophene, than does the much lower concentration of thiophene. Hence, the carbonium ion reacts with the high concentration of hydrogen chloride to form the 2-chloromethylthiophene product and not the lower concentration thiophene which would produce oligomers or polymers.

Alternatively, one can postulate that the intermediate formed from the reaction of protonated formaldehyde and thiophene is the alcohol, 2-hydroxymethylthiophene. This can react with hydrogen chloride to form the chloromethylthiophene or with thiophene to give oligomer (polymer). In this case also, a high concentration of hydrogen chloride again serves to favor the chloromethylated product over polymer.

The higher thiophene conversion may also be due to the higher concentration of protonated formaldehyde ions ($CH_2OH\oplus$) present and/or to the greater polarity of the reaction media with the high rate of gaseous hydrogen chloride addition.

The following Examples comprise illustrative embodiments of the invention and comparative processes for chloromethylthiophene production.

COMPARATIVE EXAMPLES 1-21

CMT was made in twenty runs using (100% purity basis) thiophene (2.0 moles), 70.2 g. (100% purity basis) paraformaldehyde (2.34 moles), and 3.06 moles of concentrated hydrogen chloride (32%) with a minimum of 280 rpm stirring at −5° to −10° C. Gaseous dry hydrogen chloride was added at a rate of 33.4 g./hr. (0.915 mole) over a period of three hours for a total of 100.2 g. or 2.75 moles. Then an additional 16.6 g. of hydrogen chloride (0.455 mole) was added over the course of an hour for a grand total of 116.8 g. (3.20 moles of dry hydrogen chloride) for an average gaseous addition rate of 0.4 mole HCl/mole thiophene/hour. Then 210.3 g. of cold water and a small amount of deemulsified solution were added and the quenched reaction mixture stirred an additional 3 minutes. Stirring was then stopped and the reaction mixture was held for one hour at −5° to −10° C. Two layers were formed. The layers were then separated. The CMT weight yield of the organic layer varied between 155.5 g. to 191.3 g. of CMT for the 21 different runs. The actual yields of CMT based on the amount of thiophene used, and the mole % yields of by-products 2.5 dichloromethyl thiophene, chloromethyl bis thienyl methane (CM-bis) and bis thienylmethane (bis) are shown in the attached Table 1. A statistical analysis of the data shows no significant effect of stirring speed. The overall average CMT yield was 62.7% across the 280–1300 rpm range of stirring speeds.

TABLE I

| | Mole % Yields for Examples 1-21 | | | | |
|---|---|---|---|---|---|
| | CMT | 2,5-Di | Bis | CM-Bis | Thiophene |
| 1-9a | | | | | |
| 1 | 62.9 | 2.9 | 5.0 | N.D.* | 14.2 |
| 2 | 75.3 | 3.7 | 6.0 | N.D. | 8.5 |
| 3 | 67.3 | 2.4 | 5.6 | N.D. | 14.6 |
| 4 | 62.7 | 4.9 | N.D. | N.D. | N.D. |
| 5 | 58.6 | 8.6 | 6.6 | 4.7 | 20.5 |
| 6 | 47.4 | 1.9 | 2.5 | 1.1 | 14.0 |
| 7 | 61.4 | 2.8 | 8.3 | 1.6 | 10.8 |
| 8 | 65.0 | 3.5 | 9.0 | 2.0 | 9.3 |
| 9 | 59.0 | 3.7 | 9.1 | 4.0 | 9.7 |
| 10-17b | | | | | |
| 10 | 72.1 | 4.3 | 5.4 | 2.9 | 15.2 |
| 11 | 70.7 | 7.9 | N.D. | N.D. | N.D. |
| 12 | 63.2 | 3.0 | 8.0 | 3.0 | 9.4 |
| 13 | 53.7 | 4.2 | 8.0 | 3.1 | 13.1 |
| 14 | 62.3 | 2.4 | 7.6 | 1.9 | 15.8 |
| 15 | 63.2 | 2.5 | 7.6 | 2.2 | 15.8 |
| 16 | 61.5 | 2.8 | 2.8 | 1.1 | 3.0 |
| 17 | 59.0 | 5.0 | 9.0 | 1.7 | 11.3 |
| 18-21c | | | | | |
| 18 | 64.7 | 3.1 | 7.9 | 2.8 | 11.7 |
| 19 | 60.8 | 3.5 | 5.3 | 1.7 | 15.8 |
| 20 | 61.1 | 4.3 | 6.4 | 2.1 | 8.1 |

TABLE I-continued

| | Mole % Yields for Examples 1-21 | | | | |
|---|---|---|---|---|---|
| | CMT | 2,5-Di | Bis | CM-Bis | Thiophene |
| 21 | 64.5 | 2.4 | 5.1 | 2.2 | 12.3 | a - Runs made at 280 rpm stirrer speed
b - Runs made at 500 rpm stirrer speed
c - Runs made at 1300 rpm stirrer speed
*Not determined

EXAMPLE 22

To a one liter 3 neck flask equipped with a mechanical stirrer, and a reflux condenser is charged thiophene, paraformaldehyde and aqueous hydrogen chloride in amounts as indicated.

| Material | Moles | Grams |
|---|---|---|
| Thiophene | 2.0 | 168.0 |
| Paraformaldehyde | 2.34 | 70.2 |
| 36.76% aqueous hydrogen chloride | 3.04 | 301.9 |
| Hydrogen Chloride gaseous | 3.20 | 116.8 |

Gaseous hydrogen chloride in the amount shown above was added over a two hour period (58.4 gm/hr) (0.8 moles HCl/mole thiophene/hr.) with two hours of additional stirring at −10° C. after the gaseous hydrogen chloride addition was completed.

After four hours the temperature was −7° C. Then 210.3 gm. of water and a small amount of a commercially obtained deemulsifier was added producing a small rise in temperature. The quenched reaction mixture was stirred an additional 3 minutes and then stopped. The mixture was allowed to stand 1 hour. Two distinct layers were produced. The organic layer weighed 247.4 grams, and contained 72.0 wt. % 2-chloromethylthiophene by analysis, corresponding to a yield of 70.1% based on the amount of thiophene.

EXAMPLE 23

The procedure of Example 22 was followed using the following reactants in the amounts as specified.

| Reagents | Molecular Weight | Moles | Grams |
|---|---|---|---|
| Thiophene | 84 | 2.0 | 168.0 |
| Paraformaldehyde | 30 | 2.34 | 72.4 |
| 32% aqueous hydrogen chloride | 36.5 | 3.06 | 34.9 |
| hydrogen chloride gaseous | 36.5 | 3.2 | 116.8 |

The 116.8 grams of gaseous hydrogen chloride was added over a period of 1.5 hours at a rate of 1.05 moles of hydrogen chloride per mole of thiophene per hour at a temperature of −5° C. to −10° C. followed by 2.5 hours more of stirring at this temperature and then quenching as above.

The product weighed 247 grams with a 2-chloromethylation analysis of 73.4 wt. % for a 70.7% yield based on the amount of thiophene.

EXAMPLE 24

Example 23 was repeated and the 2-chloromethylthiophene yield was 69.0%.

COMPARATIVE EXAMPLES 25 and 26

Examples 25 and 26 were similar to the above Examples 23 and 24 except that the gaseous hydrogen chloride addition (1.5 hrs.) was immediately followed by quenching. The 2-chloromethylthiophene yields were 32.0 and 40.7% based on the amount of thiophene.

The following table provides a method for comparing the process of the invention Examples 22-24 with that of the prior art as exemplified by Examples 1-21. The pertinent data is presented in Table II.

TABLE II

| Example | Gaseous HA Addition Time, hrs. | Rate of Addn. of Gaseous HCl | Additional Stirring Time, Hrs. | Mole % Yields* | | | | |
|---|---|---|---|---|---|---|---|---|
| | | | | CMT | 2,5-Di | Bis | CM-Bis | Thiophene | Polymer |
| av. of 1—21 | 4 | 0.4 | 0 | 62.7 | 3.8 | 6.6 | 2.4 | 12.3 | 12.2 |
| 22 | 2 | 1.6 | 2 | 70.1 | 5.5 | 9.2 | 3.1 | 4.1 | 8.0 |
| 23 | 1.5 | 2.1 | 2.5 | 70.7 | 3.3 | 8.7 | 1.4 | 11.3 | 4.6 |
| 24 | 1.5 | 2.1 | 2.5 | 69.0 | 5.8 | 8.7 | 1.8 | 7.9 | 6.8 |
| 25 | 1.5 | 2.1 | 0 | 32.0 | 2.7 | 1.7 | N.D. | 20.3 | N.D. |
| 26 | 1.5 | 2.1 | 0 | 40.7 | 3.7 | 2.3 | N.D. | 25.1 | N.D. |

*N.D. — not determined

What is claimed is:

1. A method of producing chloromethylthiophene comprising reacting thiophene with paraformaldehyde, gaseous hydrogen chloride and aqueous hydrochloric acid for a period of time necessary to complete the reaction and wherein the addition rate of the gaseous hydrogen chloride is from about 0.6 mole per mole of thiophene per hour to about 1.5 moles per mole of thiophene per hour.

2. The method of claim 1 wherein the total reaction time is from about 3 to about 6 hours.

3. The method of claim 1 wherein the gaseous hydrogen chloride is added at a rate of from about 1 mole of gaseous hydrogen chloride per mole of thiophene per hour.

4. The method of claim 1 wherein the total hydrogen chloride added in the process is from about 2.5 moles to about 4.0 moles per mole of thiophene.

5. The method of claim 1 wherein the molar ratio of the amount of gaseous hydrogen chloride to aqueous hydrogen chloride is from about 0.65 to about 1.45.

6. The method of claim 1 wherein the reaction is conducted at a temperature of from about −20° C. to +5° C.

7. The method of claim 1 wherein the strength of the aqueous hydrogen chloride is from about 22% to 42%.

8. The process of claim 1 wherein the reaction is allowed to continue for 1.5 to 3.5 hours after completion of the addition of the gaseous hydrogen chloride.

* * * * *